US012569331B2

(12) United States Patent
Mora et al.

(10) Patent No.: US 12,569,331 B2
(45) Date of Patent: *Mar. 10, 2026

(54) IMPLANT WITH A VISUAL INDICATOR OF A BARRIER LAYER

(71) Applicant: ESTABLISHMENT LABS S.A., Alajuela (CR)

(72) Inventors: Rolando Mora, Alajuela (CR); Salvador Dada, Alajuela (CR); Juan Jose Chacon, Alajuela (CR)

(73) Assignee: Establishment Labs S.A., La Garita (CR)

( * ) Notice: Subject to any disclaimer, the term of this patent is extended or adjusted under 35 U.S.C. 154(b) by 6 days.

This patent is subject to a terminal disclaimer.

(21) Appl. No.: 18/119,166

(22) Filed: Mar. 8, 2023

(65) Prior Publication Data

US 2023/0285138 A1     Sep. 14, 2023

Related U.S. Application Data

(63) Continuation of application No. 16/143,595, filed on Sep. 27, 2018, now Pat. No. 11,607,306, which is a
(Continued)

(51) Int. Cl.
| | |
|---|---|
| *A61F 2/12* | (2006.01) |
| *B29C 41/02* | (2006.01) |
| *B29C 41/22* | (2006.01) |

(52) U.S. Cl.
CPC ................ *A61F 2/12* (2013.01); *B29C 41/02* (2013.01); *B29C 41/22* (2013.01);
(Continued)

(58) Field of Classification Search
CPC ................ A61F 2/12; A61F 2210/0076; A61F 2250/0036; A61F 2250/005
See application file for complete search history.

(56) References Cited

U.S. PATENT DOCUMENTS 3,366,975 A     2/1968  Pangman
4,455,691 A  *  6/1984  Van Aken Redinger ...................
                                                A61F 2/12
                                                528/901
(Continued)

OTHER PUBLICATIONS

"U.S. Appl. No. 13/412,221, Advisory Action mailed Dec. 17, 2014", 3 pgs.
(Continued)

*Primary Examiner* — Suzette J Gherbi
(74) *Attorney, Agent, or Firm* — SCHWEGMAN LUNDBERG & WOESSNER, P.A.

(57) ABSTRACT

An implantable soft tissue prosthesis device comprising a silicone elastomer-shell filled with silicone gel or liquid, which among the layers that constitute its shell includes a barrier layer formed of a low permeability silicone, which impedes the bleeding or diffusion of the silicone gel from the inside of the implant to its surroundings through the shell. This barrier layer is given a coloration different to the other layers of the shell, making it visible in the finished product. The coloration of the barrier layer gives the fabricator of the implant as well as to medical personnel, the possibility to identify the presence of the barrier layer and its homogeneity, improving the safety of the device.

15 Claims, 2 Drawing Sheets

Related U.S. Application Data continuation of application No. 14/598,762, filed on Jan. 16, 2015, now Pat. No. 10,111,744, which is a continuation of application No. 13/412,221, filed on Mar. 5, 2012, now abandoned.

(60) Provisional application No. 61/449,931, filed on Mar. 7, 2011.

(52) U.S. Cl.
CPC . *A61F 2210/0076* (2013.01); *A61F 2240/001* (2013.01); *A61F 2250/0036* (2013.01); *A61F 2250/005* (2013.01)

(56) References Cited

U.S. PATENT DOCUMENTS

| | | | |
|---|---|---|---|
| 4,650,487 A | 3/1987 | Chaglassian | |
| 4,764,118 A * | 8/1988 | Touati | B29C 35/08 |
| | | | 433/229 |
| 4,773,909 A | 9/1988 | Chaglassian | |
| 4,795,463 A | 1/1989 | Gerow | |
| 4,960,425 A * | 10/1990 | Yan | A61F 2/12 |
| | | | 623/8 |
| 5,630,844 A | 5/1997 | Dogan | |
| 5,904,886 A * | 5/1999 | Stecker | B29C 41/20 |
| | | | 264/247 |
| 6,187,233 B1 | 2/2001 | Smith | |
| 8,104,097 B2 | 1/2012 | Hamann | |
| 8,562,679 B2 * | 10/2013 | Rechenberg | A61F 2/12 |
| | | | 623/8 |
| 8,708,955 B2 * | 4/2014 | Tilson | A61B 17/8855 |
| | | | 604/103.1 |
| 10,111,744 B2 * | 10/2018 | Mora | B29C 41/22 |
| 11,045,307 B2 * | 6/2021 | Quirós | B29C 33/424 |
| 11,109,956 B2 * | 9/2021 | Chacon Quiros | A61F 2/12 |
| 11,607,306 B2 | 3/2023 | Mora et al. | |
| 11,672,648 B2 * | 6/2023 | Garcia | A61F 2/12 |
| | | | 623/8 |
| 2005/0044609 A1 * | 3/2005 | Vistins | B32B 27/30 |
| | | | 2/159 |
| 2005/0079365 A1 * | 4/2005 | Widenhouse | B05D 3/101 |
| | | | 427/551 |
| 2005/0149186 A1 * | 7/2005 | Roballey | A61F 2/12 |
| | | | 623/8 |
| 2007/0104904 A1 * | 5/2007 | Hamann | B32B 25/00 |
| | | | 428/35.7 |
| 2008/0243167 A1 | 10/2008 | Paganon et al. | |
| 2008/0269555 A1 | 10/2008 | Paganon et al. | |
| 2009/0030515 A1 * | 1/2009 | Schuessler | A61F 2/12 |
| | | | 623/8 |
| 2009/0126074 A1 | 5/2009 | Mattesky | |
| 2009/0162533 A1 | 6/2009 | Kirby et al. | |
| 2009/0236771 A1 | 9/2009 | Mitchell et al. | |
| 2009/0299374 A1 | 12/2009 | Tilson et al. | |
| 2009/0299401 A1 | 12/2009 | Tilson | |
| 2009/0301643 A1 * | 12/2009 | Tilson | A61M 29/02 |
| | | | 156/212 |
| 2010/0028396 A1 * | 2/2010 | Ward | A61F 2/0059 |
| | | | 623/23.72 |
| 2010/0076437 A1 | 3/2010 | Tilson et al. | |
| 2010/0152654 A1 | 6/2010 | Tilson et al. | |
| 2010/0241152 A1 | 9/2010 | Tilson et al. | |
| 2010/0241153 A1 | 9/2010 | Tilson et al. | |
| 2010/0241178 A1 | 9/2010 | Tilson et al. | |
| 2010/0257657 A1 | 10/2010 | Hamann et al. | |
| 2010/0262218 A1 | 10/2010 | Deshmukh | |
| 2011/0054636 A1 | 3/2011 | Gill | |
| 2012/0124714 A1 * | 5/2012 | Hamann | B32B 25/00 |
| | | | 2/168 |
| 2012/0232652 A1 * | 9/2012 | Mora | A61F 2/12 |
| | | | 623/8 |
| 2013/0096676 A1 * | 4/2013 | Boegershausen | A61F 2/12 |
| | | | 623/8 |
| 2015/0150675 A1 * | 6/2015 | Mora | B29C 41/02 |
| | | | 264/40.1 |
| 2019/0099260 A1 | 4/2019 | Mora et al. | |
| 2021/0259823 A1 * | 8/2021 | Garcia | A61F 2/12 |
| 2021/0346150 A1 * | 11/2021 | Chacón Quirós | B29C 33/424 |
| 2022/0055258 A1 * | 2/2022 | Fei | B29C 41/22 |
| 2022/0185872 A1 * | 6/2022 | Medof | G01N 33/564 |

OTHER PUBLICATIONS

"U.S. Appl. No. 13/412,221, Examiner Interview Summary mailed Nov. 1, 2013", 4 pgs.
"U.S. Appl. No. 13/412,221, Final Office Action mailed Jul. 16, 2014", 9 pgs.
"U.S. Appl. No. 13/412,221, Final Office Action mailed Sep. 5, 2013", 11 pgs.
"U.S. Appl. No. 13/412,221, Non Final Office Action mailed Feb. 19, 2013", 13 pgs.
"U.S. Appl. No. 13/412,221, Non Final Office Action mailed Oct. 23, 2012", 11 pgs.
"U.S. Appl. No. 13/412,221, Notice of Non-Compliant Amendment mailed Jul. 24, 2013", 2 pgs.
"U.S. Appl. No. 13/412,221, Response filed Feb. 4, 2014 to Final Office Action mailed Sep. 5, 2013", 8 pgs.
"U.S. Appl. No. 13/412,221, Response filed Jul. 10, 2013 to Non Final Office Action mailed Feb. 19, 2013", 10 pgs.
"U.S. Appl. No. 13/412,221, Response filed Jul. 24, 2013 to Notice of Non-Compliant Amendment mailed Jul. 24, 2013", 10 pgs.
"U.S. Appl. No. 13/412,221, Response filed Dec. 12, 2014 to Final Office Action mailed Jul. 16, 2014", 10 pgs.
"U.S. Appl. No. 14/598,762, Final Office Action mailed Apr. 19, 2018", 7 pgs.
"U.S. Appl. No. 14/598,762, Final Office Action mailed Oct. 21, 2016", 9 pgs.
"U.S. Appl. No. 14/598,762, Non Final Office Action mailed Jan. 11, 2016", 7 pgs.
"U.S. Appl. No. 14/598,762, Non Final Office Action mailed Jul. 13, 2017", 9 pgs.
"U.S. Appl. No. 14/598,762, Notice of Allowance filed Jun. 27, 2018", 10 pgs.
"U.S. Appl. No. 14/598,762, Preliminary Amendment filed Jan. 16, 2015", 6 pgs.
"U.S. Appl. No. 14/598,762, Response filed Mar. 21, 2017 to Final Office Action mailed Oct. 21, 2016", 15 pgs.
"U.S. Appl. No. 14/598,762, Response filed Jun. 14, 2018 to Final Office Action mailed Apr. 19, 2018", 9 pgs.
"U.S. Appl. No. 14/598,762, Response filed Jul. 8, 2016 to Non Final Office Action mailed Jan. 11, 2016", 12 pgs.
"U.S. Appl. No. 14/598,762, Response filed Dec. 13, 2017 to Non Final Office Action mailed Jul. 13, 2017", 13 pgs.
"U.S. Appl. No. 16/143,595, Non Final Office Action mailed Jul. 5, 2022", 9 pgs.
"U.S. Appl. No. 16/143,595, Notice of Allowance mailed Nov. 17, 2022", 5 pgs.
"U.S. Appl. No. 16/143,595, Preliminary Amendment filed Sep. 27, 2018", 3 pgs.
"U.S. Appl. No. 16/143,595, Response filed Oct. 5, 2022 to Non Final Office Action mailed Jul. 5, 2022", 10 pgs.
"U.S. Appl. No. 16/143,595, Supplemental Preliminary Amendment filed Jun. 3, 2022", 6 pgs.
"U.S. Appl. No. 16/143,595, Supplemental Preliminary Amendment filed Dec. 26, 2018", 7 pgs.

* cited by examiner

IMPLANT WITH A VISUAL INDICATOR OF A BARRIER LAYER

CROSS-REFERENCE TO RELATED APPLICATIONS

This application is a continuation of U.S. application Ser. No. 16/143,595, filed on Sep. 27, 2018, which is a continuation of U.S. application Ser. No. 14/598,762, filed on Jan. 16, 2015, now issued as U.S. Pat. No. 10,111,744, which is a continuation of U.S. application Ser. No. 13/412,221, filed on Mar. 5, 2012. which claims the benefit under 35 U.S.C. § 119 to U.S. Provisional Application No. 61/449,931 filed on Mar. 7, 2011, all of which are incorporated herein by reference in their entireties.

BACKGROUND OF THE INVENTION

This invention relates to an implantable prosthesis, comprising a multilayer molded elastomer shell, from which one or more of the layers are made of an elastomer with different chemical or physical properties, and which is afterwards filled with a liquid or a gel. Particularly, this invention relates to a prosthesis in which the differentiated layers are made visible by means of fabricating them with a different color material, so the differentiated layers can be easily identified in the final product by mere observation, providing a greater degree of safety of the device.

Today, the augmentation and reconstruction of the human breast requiring the use of an implant, as well as the use of soft tissue implants in other parts of the human body, have become a fairly common practice in the craft of plastic and reconstructive surgery. Typical long-term implantable devices, which are often selected for these procedures, include round, anatomical or molded silicone gel filled shapes. In recent years, the implants used for these procedures have raised concern with respect to the possibility of silicone gel bleeding through the implant shell after the implantation procedure. This concern was addressed in the prior art by the inclusion of a low diffusion barrier layer that would impede or diminish the bleeding or diffusion of the low molecular silicone particles of the silicone filler through the shell.

Conventional silicone implant shells are multilayered. Specifically, such shells include several layers and one or more inner barrier layers which are able to substantially resist gel bleeding, usually sandwiched between the outer and inner layers, but which may be located in any position in the shell structure. Some of the silicone filled breast implants include a low diffusion silicone elastomer shell made with layers of a dimethyl-diphenyl silicone elastomer, having a diphenyl polymer mole percentage of around 5%, and a barrier layer of dimethyl-diphenyl silicone elastomer having a diphenyl polymer mole percentage of around 15%. Fluor and other chemistries are also used as low diffusion silicone elastomer layers.

U.S. Pat. No. 4,455,691 discloses a gel-filled breast implant including a layered silicone elastomer shell made with outer layers of a dimethyl silicone elastomer and an intermediate barrier layer made of the reaction product of polydimethylsiloxane and either 3,3,3-trifluoropropylpolysiloxane, diphenylpolysiloxane or methylphenylpolysiloxane.

European Patent EP0030838 describes a silicone gel-filled silicone rubber article which is a flexible silicone rubber container filled with a silicone gel composition that includes an essentially continuous barrier layer of a fluorine-containing organopolysiloxane located between the container wall and the silicone gel composition to reduce the tendency of unreacted components present in the silicone gel to exude or bleed to the surface of the article.

Even though the performance of such barrier layers is considered acceptable at their present state of development, a serious problem persists in the use of this devices, both at the manufacturing and operating room levels, which is the impossibility for quality control personnel and medical staff of easily identifying the presence of the important low diffusion barrier layers within the complete prosthesis, without the use of impractical specialized equipment or without the use of destructive tests.

The same situation exists for many soft tissue implants where the same general fabrication technics are employed, i.e. breast, calf, gluteus, penile, testicular, nasal implants, and tissue expanders.

BRIEF SUMMARY OF THE INVENTION

The present invention provides an implantable device consisting of a flexible elastomer shell enclosing an internal lumen, which is filled with a liquid or gel. The shell includes multiple layers of an elastomer of which the innermost layer comes in direct contact with the filler. One or more of the layers included in the shell structure are made with a different material that will substantially impede the diffusion or bleeding of the filling material particles through the implant shell. These layers are given an identifiable coloration in order to differentiate them from the other layers. The coloration of the barrier layers allows a series of advantages over traditional implants, including the possibility of visually identifying the existence of the barrier layer in each implant, as well as the correct and homogenous application of the same. This also allows the possibility of including the control of the barrier layer as a simpler part of the quality control process in the fabrication of the implants, and allows the medical professionals who have the responsibility of employing such implants in surgical procedures to verify the presence and correctness of the barrier layer by simple observation.

BRIEF DESCRIPTION OF THE SEVERAL VIEWS OF THE DRAWINGS

Certain characteristics and advantages of the present invention may be more clearly understood with reference to the following description in conjunction with the accompanying drawings of which.

Figure 1:
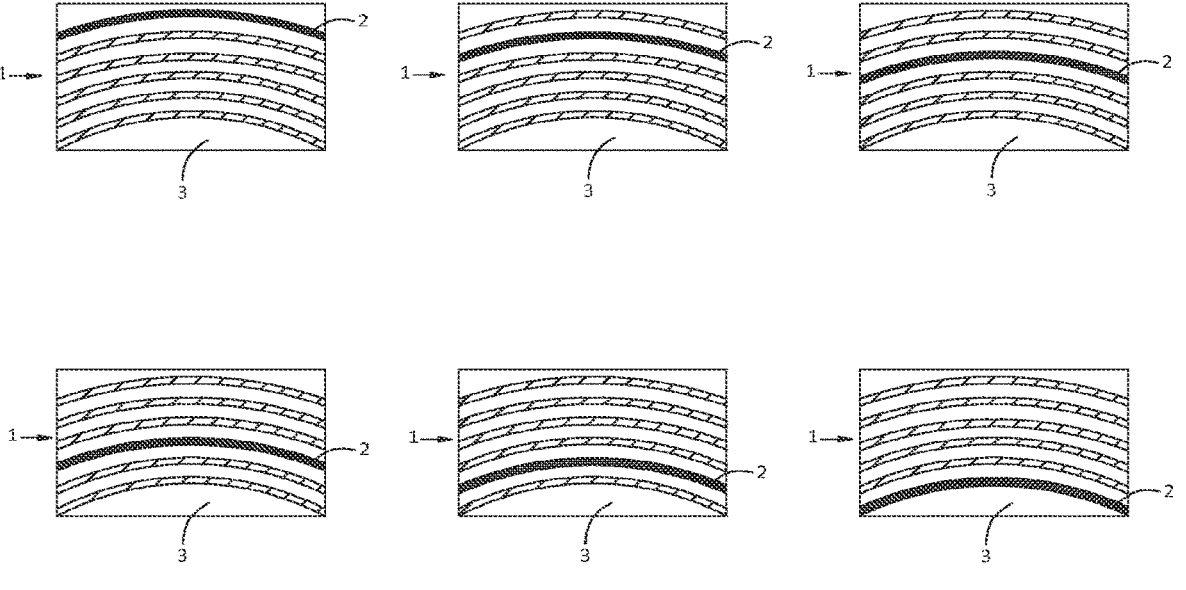
FIG. 1. Incorporates six possible examples of cross-sectional views through portions of implants of the present invention, having a multilayer shell 1 and a colored barrier layer 2 which can be found at any position of the shell, either on top, bottom or nestled between the other layers. The lumen 3 shall be occupied by the corresponding filler material.
Figure 2:
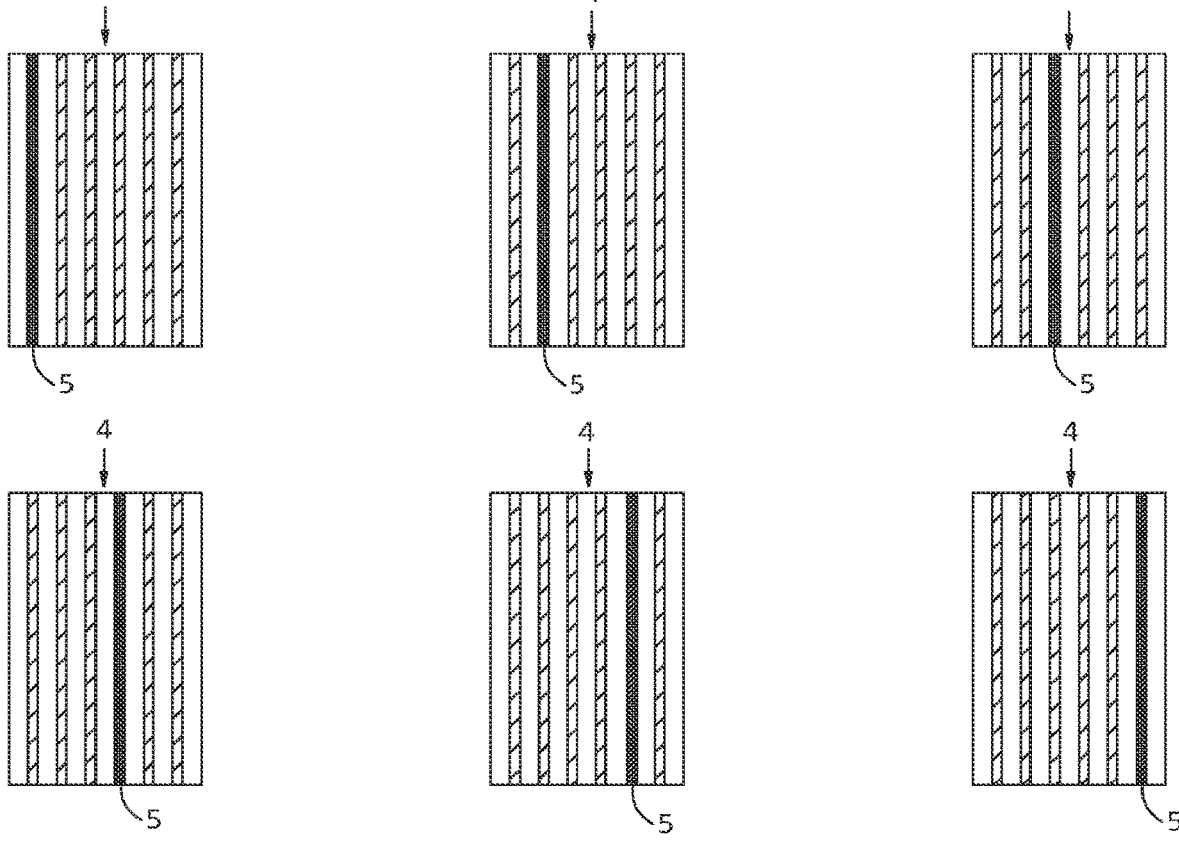
FIG. 2. Incorporates six possible examples of vertical cross-sectional views through portions of the implant shells of the present invention, having a multilayer shell 4 and one colored barrier layer 5 which can be found at any position of the shell, either on top, bottom or nestled between the other layers.

It is important to note that the number of layers included in the drawings is just an example, since the shell structure in an implant may consist of any number of layers, of which the low diffusion barrier layers incorporating the coloration may be one or more and located anywhere in the structure.

DETAILED DESCRIPTION OF THE INVENTION

The present invention provides a gel or liquid-filled implant, typically consisting of an internal silicone gel and a flexible elastomer shell enclosing the gel. The shell includes multiple layers of a silicone elastomer of which the innermost layer comes in direct contact with the filling. The multilayer shell structure includes one or more low diffusion barrier layers from which at least one shall have a color different to the other layers. The present invention is based on the fact that the low diffusion barrier layers present in the flexible shells of silicone implantable devices currently available in the market are colorless. Consequently, it is not possible for the health professionals to unequivocally establish its presence, integrity and/or uniformity during the product examination at the operating room. It is also very difficult for quality control personnel to identify these same characteristics on assembled implants during the fabrication process.

More specifically, the shell is defined as a multilayer structure in which a colored low diffusion barrier layer is either nestled between, or laid on top or below the standard elastomer layers. The barrier layer is usually a silicone elastomer comprising a polysiloxane backbone and having a minimum mole percentage of 10% of a substituted or pendant chemical group that retards permeation of silicone through the layer. The silicone elastomer usually present in the low diffusion barrier layer is a polydimethylsiloxane and the pendant chemical group is one of a phenyl or fluorine group, for example, a diphenyl group or a methylphenyl group, a trifluorpropyl group, and mixtures thereof.

Usually, the shell itself as well as the individual layers, both the colored barrier and the standard ones, have a uniform thickness. The total thickness usually ranges from about 0.33 mm to about 1.00 mm, but may vary upwards or downwards from these figures.

Advantageously, the use of a barrier layer on the implant manufacturing promotes the reduction of gel bleeding through the shell; in most cases the diphenyl or fluorine group are located in the middle of the multilayer shell. In currently available implants the diphenyl layer is uncolored, just as the dimethyl layers. This makes impossible to distinguish the presence of this important barrier layer in the finished product.

Process wise, in the manufacturing of the implants now on the market, there may be in-process controls to verify the presence of the barrier layer using an optical comparator. This control is established because it is feasible that an operator may forget to apply the barrier layer to a shell; if one implant is assembled without the barrier layer, it will be almost impossible for the surgeons to determine whether the prosthesis to be implanted has the low diffusion barrier layer or not.

Usefully, this invention allows to visually confirm the presence and homogeneity of the bleed resistant layer around the implant, which is almost invisible in the implants currently in the market.

The surgeon with this invention can unequivocally confirm the presence of a low diffusion layer by means of the visual aid.

The step of forming a colored dispersion to manufacture the colored low diffusion barrier layer may consist of adding pigments dispersed in a vinyldimethyl-terminated polydimethylsiloxane polymer. The colored dispersion shall be the dispersion containing the additional diphenyl group or fluor or any other chemistry used for gel diffusion reduction or control. The dispersion itself may be also fabricated in a material which itself may be of a different color, or a chemical agent may be added which would change the color of the material.

In a specific embodiment, the present implants are suitable for implantation in the human body and the flexible colored shell is accordingly sized and shaped.

Several systems and methods can be used for constructing a silicone implant elastomeric shell and they are contemplated in this invention. The step of forming the shell comprises coating a mold with a dispersed or liquid elastomer; the shell may be formed by dipping, spraying, pouring, blowing or rotational molding, using a suitably shaped mold, coated with dispersion of a silicone elastomer and a solvent, allowing the solvent to evaporate, and allowing the elastomer to cure, as it is contemplated and employed in the existing art.

What we claim is:

1. An implantable soft tissue prosthesis device comprising:
   a multilayer shell having one or more layers, the multilayer shell including a silicone elastomer, including:
   the multilayered shell enclosing a lumen filled with at least one of a fluid or a gel;
   wherein at least one layer of the multilayer shell includes a homogenous low diffusion barrier layer, the homogeneous low diffusion barrier layer nestled between at least two layers of the one or more layers; and
   wherein the homogenous low diffusion barrier layer includes one or more pigments dispersed in a vinyldimethyl-terminated polydimethylsiloxane polymer.

2. The implantable soft tissue prosthesis device of claim 1, wherein the at least one of the fluid or the gel includes a silicone.

3. The implantable soft tissue prosthesis device of claim 1, wherein the one or more pigments is different than other layers of the multilayer shell.

4. The implantable soft tissue prosthesis device of claim 1, wherein the multilayer shell includes the one or more layers formed from an elastomer.

5. The implantable soft tissue prosthesis device of claim 1, wherein each layer of the multilayer shell has a uniform thickness.

6. The implantable soft tissue prosthesis device of claim 1, wherein the homogenous low diffusion barrier layer is visible by a health professional.

7. A multilayered, flexible implant, comprising:
   a shell having one or more layers, surrounding a lumen, including:
   at least one elastomer layer; and
   a low diffusion barrier layer nestled between at least two layers of the one or more layers, the low diffusion barrier layer having a color different than the at least one elastomer layer and formed from a material including polydimethylsiloxane and a pendant chemical group including one of a phenyl or fluorine group;
   wherein the low diffusion barrier layer includes a color dispersion including diphenyl group; and
   a liquid or gel disposed within the lumen of the shell.

8. The multilayered, flexible implant of claim 7, wherein the low diffusion barrier layer is in contact with the liquid or gel.

9. The multilayered, flexible implant of claim 7, wherein the at least one elastomer layer is made of a silicone elastomer.

10. The multilayered, flexible implant of claim 7, wherein the low diffusion barrier layer is visible by observation by health professionals.

11. The multilayered, flexible implant of claim 7, wherein the pendant chemical group includes a fluorine group.

12. The multilayered, flexible implant of claim 7, wherein the low diffusion barrier layer includes a pigment dispersed in a vinyldimethyl-terminated polydimethylsiloxane polymer.

13. The multilayered, flexible implant of claim 7, wherein the multilayered, flexible implant is a breast implant.

14. The multilayered, flexible implant of claim 7, wherein each layer of the one or more layers and the shell has a uniform thickness.

15. The multilayered, flexible implant of claim 7, wherein the low diffusion barrier layer is formed from a silicone elastomer comprising a polysiloxane backbone and having a minimum mole percentage of 10% of a substituted or pendant chemical group that is configured to minimize permeation of silicone from the lumen.

\* \* \* \* \*